United States Patent
Bernard et al.

(10) Patent No.: US 8,631,716 B2
(45) Date of Patent: Jan. 21, 2014

(54) CONNECTION OF AN ACCESSORY TO A VESSEL

(75) Inventors: Frederic Bernard, La Cadiere d'Azur (FR); Eric Chevalier, Paris (FR)

(73) Assignee: Sartorius Stedim Biotech, Aubagne (FR)

( * ) Notice: Subject to any disclaimer, the term of this patent is extended or adjusted under 35 U.S.C. 154(b) by 536 days.

(21) Appl. No.: 12/744,941

(22) PCT Filed: Nov. 24, 2008

(86) PCT No.: PCT/FR2008/052117
§ 371 (c)(1),
(2), (4) Date: May 27, 2010

(87) PCT Pub. No.: WO2009/071829
PCT Pub. Date: Jun. 11, 2009

(65) Prior Publication Data
US 2010/0301060 A1    Dec. 2, 2010

(30) Foreign Application Priority Data
Nov. 27, 2007 (FR) ...................................... 07 08293

(51) Int. Cl.
*G01D 11/24* (2006.01)
*G01L 19/14* (2006.01)

(52) U.S. Cl.
CPC .............. *G01D 11/245* (2013.01); *G01L 19/14* (2013.01)
USPC .......................................... 73/866.5; 73/431

(58) Field of Classification Search
USPC ................................. 73/866.5, 431
See application file for complete search history.

(56) References Cited

U.S. PATENT DOCUMENTS 3,625,850 A * 12/1971 Arrington ...................... 204/402
3,904,960 A *  9/1975 Niehaus ........................ 324/696

(Continued)

FOREIGN PATENT DOCUMENTS

DE    25 57 542    6/1977
DE    42 07 845    9/1993

(Continued)

OTHER PUBLICATIONS

International Search Report Jun. 5, 2009, from corresponding PCT application.

*Primary Examiner* — David A Rogers
(74) *Attorney, Agent, or Firm* — Young & Thompson

(57) ABSTRACT

A device for connecting to a vessel an accessory has an active portion that includes a first, second and third member and a chamber. The first member ensures rigid attachment of the device to the vessel, defines a passageway, acts as a holder for the second member and as a translation guide between a first distal state and a second proximal state, contributes as a guide for the third member and participates in defining the chamber. The second member acts as a holder for the third member rigidly attached thereon, defines a mobile member capable of sliding between the first distal state and the second proximal state. The third member includes a head, and acts as a holder for the accessory rigidly attached thereon, defines a mobile member capable of sliding between the first distal state and the second proximal state, ensures in the first distal state the tight closing of the opening using the head, ensures in the second proximal state a protection of the active proximal portion using the head, and participates in defining the chamber.

9 Claims, 7 Drawing Sheets

(56) References Cited

U.S. PATENT DOCUMENTS

| | | | |
|---|---|---|---|
| 4,096,754 A * | 6/1978 | Beveridge et al. | 73/866.5 |
| 4,491,018 A * | 1/1985 | Stringer et al. | 73/865.8 |
| 4,852,385 A | 8/1989 | Brinkmann | |
| 5,727,498 A * | 3/1998 | Hackler et al. | 116/206 |
| 5,939,610 A * | 8/1999 | Iwamoto et al. | 73/1.03 |
| 5,962,795 A * | 10/1999 | Lambert | 73/866.5 |
| 5,988,422 A | 11/1999 | Vallot | |
| 6,091,489 A * | 7/2000 | Welker | 356/241.1 |
| 6,131,473 A * | 10/2000 | Hoffman et al. | 73/866.5 |
| 6,374,685 B1 * | 4/2002 | Daly | 73/866.5 |
| 6,640,658 B1 * | 11/2003 | Guerrero et al. | 73/866.5 |
| 7,121,158 B2 * | 10/2006 | Scott et al. | 73/866.5 |
| 7,325,555 B2 * | 2/2008 | Caderas | 134/64 R |
| 7,472,615 B2 * | 1/2009 | Mayeaux | 73/866.5 |
| 7,594,449 B2 * | 9/2009 | Tottewitz et al. | 73/866.5 |
| 7,631,569 B2 * | 12/2009 | Salo | 73/866.5 |
| 7,674,254 B2 | 3/2010 | Baumfalk et al. | |
| 7,980,132 B2 * | 7/2011 | Gustin | 73/431 |
| 2002/0144559 A1 * | 10/2002 | Bueno Harto et al. | 73/866.5 |
| 2003/0019308 A1 * | 1/2003 | Oppermann et al. | 73/866.5 |
| 2004/0149039 A1 * | 8/2004 | Cardelius | 73/570 |
| 2005/0072253 A1 * | 4/2005 | Scott et al. | 73/866.5 |
| 2005/0239198 A1 | 10/2005 | Kunas et al. | |
| 2005/0239199 A1 | 10/2005 | Kunas et al. | |
| 2007/0029007 A1 * | 2/2007 | Hutchinson | 141/330 |
| 2007/0034028 A1 * | 2/2007 | Tottewitz et al. | 73/866.5 |
| 2009/0211357 A1 * | 8/2009 | Pinto et al. | 73/335.02 |
| 2010/0071472 A1 * | 3/2010 | Nakamura et al. | 73/632 |
| 2010/0089187 A1 * | 4/2010 | Yin et al. | 73/866.5 |
| 2010/0126288 A1 * | 5/2010 | Osswald | 73/866.5 |

FOREIGN PATENT DOCUMENTS

| | | |
|---|---|---|
| DE | 10 2004 015 703 | 11/2005 |
| DE | 10 2006 005 533 | 8/2007 |
| GB | 1 564 546 | 4/1980 |
| WO | 86/17151 | 12/1986 |
| WO | 00/04131 | 1/2000 |

* cited by examiner

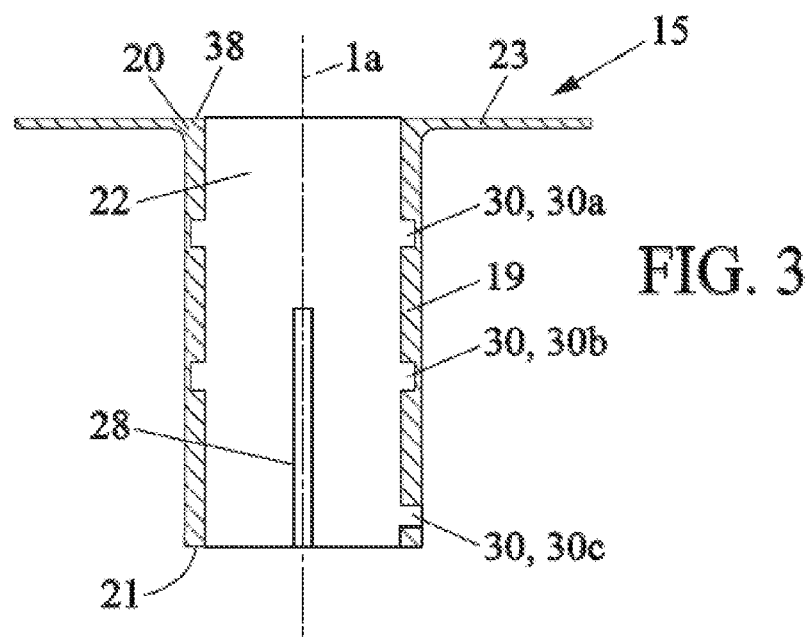
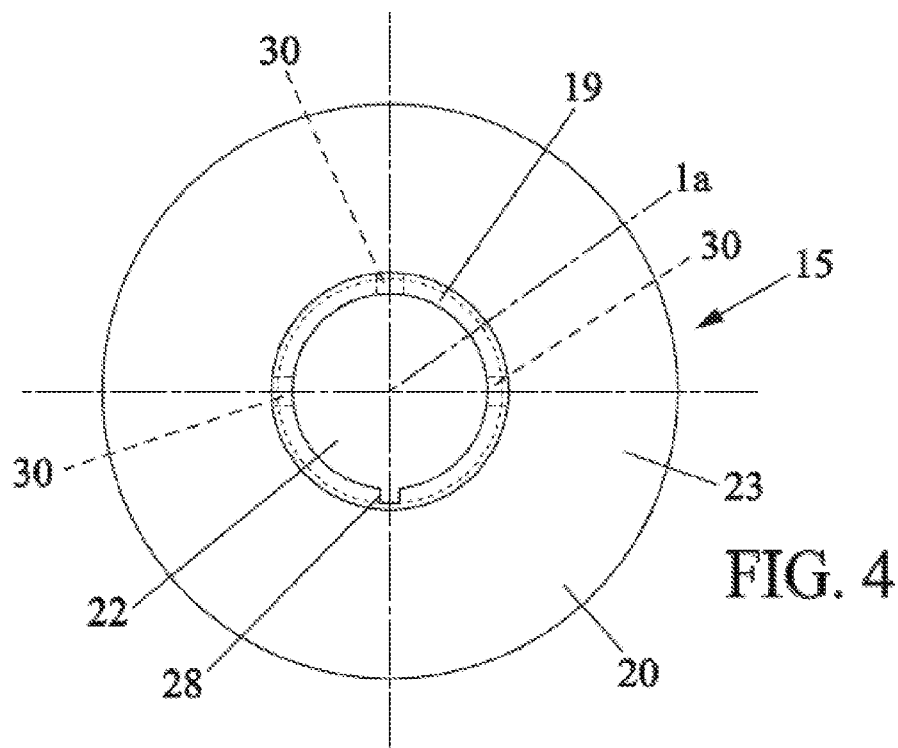

CONNECTION OF AN ACCESSORY TO A VESSEL

BACKGROUND OF THE INVENTION

1. Field of the Invention

The invention relates to the connection of an accessory to a receptacle.

More especially, its purpose is a device for connection to a receptacle of an accessory whose active proximal part is able to be put into communication with the inside of the receptacle by means of an opening of the receptacle; whereby a first unit comprises a connecting device and an accessory; whereby a second unit comprises the first unit and a receptacle comprises an opening in which the connecting device is mounted; a process for mounting the second unit; and a process for implementing the second unit.

In this case, the receptacle in question is a receptacle for storage and/or for treatment of contents such as a biopharmaceutical product. In this case, such a receptacle is understood to be a reusable rigid receptacle or a disposable flexible receptacle such as a pocket.

2. Description of the Related Art

This pocket can be a so-called 2D pocket, such as the one marketed by Sartorius Stedim Biotech under the trademark Flexboy®, whose volume can typically be between 50 milliliters and 50 liters.

The document WO 00/04131 describes such a flexible receptacle whose volume can exceed—and generally does exceed—50 liters. Such a receptacle is commonly called a 3D pocket. It is then known that rigid means for holding the pocket from the outside, at least when it comprises its contents, are associated with this pocket.

In this case, a biopharmaceutical product is understood to be one (or several) product(s) that are obtained from biotechnology—culture media, cellular cultures, buffer solutions, artificial nutrition liquids, blood products and derivatives of blood products—or a pharmaceutical product or more generally a product that is designed to be used in the medical field. Such a product is in liquid, pasty, or powdery form in one or more phases that may or may not be homogeneous. The invention also applies to products other than biopharmaceutical products, according to the definition that was just given, but is subject to analogous requirements regarding their storage or their treatment.

In this case, the accessory is understood to be a probe for measuring parameters that are relative to the contents of the receptacle, such as pressure, pH, temperature, colorimetry, conductimetry, etc., or else a filling tube or a drainage tube. The invention also applies to other accessories but those whose purpose is to be connected to a receptacle by being put into communication with the inside of the latter.

In the field of biopharmacy, it is common to use receptacles as the site for carrying out chemical or biological reactions, and, if necessary, to follow and/or monitor them, or else as a storage means. So as to prevent germs from penetrating inside the receptacle, it is important that the environment be closed, sterile and aseptic, without contact with the outside environment.

The reactions in general should take place under determined and monitored conditions (pressure, pH, temperature, colorimetry, conductimetry, etc.) or the storage should be implemented under controlled conditions. It is therefore necessary to carry out measurements or monitoring of parameters that characterize the product that is contained in the receptacle more or less frequently. These measurements should be carried out under aseptic conditions, for the reasons indicated above.

The document DE 10 2004 015703 describes a device for connecting an accessory to a receptacle that comprises two elements that are provided with guide means and hooks. This device comprises neither a third element to which the accessory is intended to be attached and that comprises a protective top and a base, nor a chamber.

The document DE 42 07 845 describes a support device for an analytical electrode, comprising a stationary outer tube, a moving, sliding inner tube, and a unit that is mounted transversely and that includes a piston that is mounted in a casing, whereby this unit can form an airtight inlet for the inner tube so as to be able to withdraw the electrode from the receptacle in which it is intended to be placed, without losing the contents of the latter. The purpose of this device is not the composition of a functional chamber.

The document WO 86/07 151 describes a maintenance device for the calibration and the automatic cleaning of a probe that is part of a continuous measuring system of the chemical or biological process, consisting in analyzing parameters of the fluid that is to be investigated.

The document DE 25 57 542 describes a measuring device for electrical values of media that flow, with measuring detectors that are placed in passage chambers, in which the passageway of a valve body forms the passage chamber and the detector is mounted in the latter.

The document US2005/0239199 describes a probe according to a particular arrangement.

The document US2005/0239198 describes a sterile and aseptic connection by means of two elements, a first element that is attached to the receptacle and a second element that can be connected to the first element. The first element comprises, at its free end, a connecting means that is provided with a cover. The second element comprises a probe that is placed inside a flexible sleeve that is provided with a connecting means that is provided with a cover, whereby the connecting means of the second element is designed to be connected to the connecting means of the first element after their respective covers are removed. The probe is attached to the receptacle by sliding the connecting means of the second element into the connecting means of the first element. The end of the probe is then inserted inside the receptacle by compression of the sleeve, whereby the probe slides inside the first element until it reaches the inside of the receptacle.

There is therefore a need for ensuring an airtight connection of an accessory to a receptacle, an easy and quick insertion of the accessory into the receptacle, and, if necessary, a calibration of the accessory when the latter is a probe, and a permanent protection of the accessory. This requirement should be satisfied with a simple device and by means of a process for easy and risk-free implementation.

BRIEF SUMMARY OF THE INVENTION

For this purpose, according to a first aspect, the purpose of the invention is a device for connection to a receptacle of an accessory whose active proximal part is able to be put into communication with the inside of the receptacle by means of an opening of the receptacle, whereby the device comprises a first element, a second element, a third element, and a chamber, in which:

The first element has the following functions:
  Ensuring the rigid attachment of the connecting device to the receptacle, Defining a channel between the inside and the outside of the receptacle, Serving as a support for the second element and an axial movement guide on an axial course C of which the two ends of travel correspond to a first distal state and a second proximal state, Helping to serve as a guide for the third element, Helping to delimit the chamber, The second element has the following functions:

Serving as a support to the third element, which is attached rigidly to it,

Forming a moving, axially sliding element on the course C whose two ends of travel correspond to the first distal state and the second proximal state, The third element, to which a top belongs, has the following functions:

Serving as a support to the accessory, which is attached rigidly to it,

Forming a moving, axially sliding element on the course C whose two ends of travel correspond to the first distal state and the second proximal state, In the first distal state, ensuring, using the top, the airtight closing of the opening, In the second proximal state, ensuring, using the top, a protection of the active proximal part, Helping to delimit the chamber, The chamber is closed in an airtight manner in the first distal state and is in communication with the inside in the second proximal state and has the function of housing the active proximal part inside or placing it on the periphery, and if necessary, Putting a storage liquid therein, Putting a liquid for regulating, monitoring and calibrating the accessory therein or constituting a chamber that is closed in an airtight manner in which the accessory is placed on standby for use.

According to one embodiment, in the first distal state, the second element is laterally opposite the first element, without being opposite a part of the first element that is adjacent to its proximal end, a part of the second element projecting from the distal end of the first element, and, in the second proximal state, the second element is laterally completely opposite the first element toward its distal end, without being opposite an axially shorter part of the first element that is adjacent to its proximal end.

According to one embodiment, the third element comprises a base and a body in addition to the top, Whereby the top has the following functions:

In the first distal state, closing the first element in an airtight manner,

In the second proximal state, helping to protect the active proximal part,

Whereby the base has the following functions:

Serving as a support to the accessory, which is attached rigidly to it,

Ensuring the guiding of the sliding, with sealing, of the third element on and relative to the first element, Helping to delimit the chamber, Whereby the body comprises a connecting part that is provided with a bore in which the accessory is inserted and at least one carrying element, rigidly connecting the top and the base.

According to one embodiment, the base comprises:

In its proximal end part, at least a first ring, capable of being able to slide axially, with sealing, by its outside surface, on and along the inside surface of the tubular wall of the first element, At its distal end part, a second ring, able to be attached rigidly by its outside surface on and against the inside surface of the tubular wall of the second element, Whereby inside surfaces of the rings are able to make possible the rigid attachment, with sealing, of the accessory.

According to a second aspect, the purpose of the invention is a first unit that comprises a connecting device and a disposable accessory, comprising an active proximal part, attached rigidly to the third element, whereby the active proximal part is housed inside or placed at the periphery of the chamber.

According to the embodiments, the distal part of the accessory projects in a distal manner from the distal end of the second element; and/or at least one other functional part, placed beside or close to the accessory, is functionally associated with the accessory; and/or the functional part is at least one tube and more especially at least two tubes, one for intake and the other for drainage.

In an embodiment such as the one that corresponds to the case where the accessory is a probe, the functional part preferably comprises at least two tubes, one for intake and calibration, and the other for drainage and rinsing.

According to the embodiments, the accessory is at least one probe or at least one tube.

According to a third aspect, the purpose of the invention is a second unit that comprises the first unit and a receptacle that comprises an opening in which the connecting device is mounted.

According to the embodiments, the receptacle is rigid and reusable or flexible and disposable, such as a so-called 3D pocket.

According to a fourth aspect, the purpose of the invention is a process for mounting the second unit, in which:

A receptacle that is devoid of contents, the accessory, and constituent elements of the connecting device are used, In a preliminary stage, the first element is attached rigidly to the receptacle at the location of the opening, In another preliminary stage, the accessory is inserted into the third element, and it is attached rigidly to the latter, In a second subsequent stage, the unit that consists of the third element+accessory is mounted on and in the second element, In a third stage, the unit that consists of second element+third element+accessory is mounted on and in the first element until the slot(s) and lug(s) work together corresponding to the first distal state.

According to the embodiments, the following are provided: an additional successive stage in which the air (or the gas) that is located in the chamber is drawn in, and it is drained from the latter; an additional successive stage in which a storage liquid is injected into the chamber; an additional successive stage in which sterilization of the unit that consists of receptacle+connecting device+accessory is initiated; and an additional successive stage in which the packaging of the unit that consists of receptacle+connecting device+accessory is initiated.

According to a fifth aspect, in a process for implementation of the second unit, operating stages that are linked specifically to the connecting device and to the accessory that comprise the following operating states are implemented:

With the chamber being empty, pass the unit that consists of the connecting device+accessory from the first distal state to the second proximal state.

Then, implement the accessory.

According to one embodiment, the process comprises an additional operation for regulating, monitoring or calibrating the accessory.

According to one embodiment, regarding the additional operational stage, a calibration of the accessory is involved, whereby the latter is then a probe with which is associated one (or, as disclosed above, two) tube(s), whereby this calibration is carried out by means of the chamber.

According to one embodiment, a single calibration or several calibrations are implemented, such as an initial calibration, a final calibration, and, if necessary, an intermediate calibration.

A calibration is implemented whereas the unit that consists of connecting device+probe+tube is in the first distal state and the chamber is closed in an airtight manner.

According to one embodiment, the process for implementation comprises a preliminary operating stage that consists in draining the chamber of the storage liquid that was put there during production, and then, if necessary, rinsing it.

A calibration is implemented by the following stages:
First, a calibration solution is injected into the chamber that is closed in an airtight manner,
Then, with the calibration solution filling up the chamber that is still closed in an airtight manner and with the active proximal part being in contact with the calibration solution, the probe is calibrated if necessary and as required,
Then, with the chamber still being closed in an airtight manner, the calibration solution is drained,
Then, the chamber is rinsed, and it is drained.

The invention makes it possible in particular to be able to store, to calibrate, and to use a disposable probe under conditions that may or may not be sterile.

The invention is most particularly applicable in the biopharmaceutical field, for example for applications linked to mixing, for disposable bioreactors, and for thermoregulation.

BRIEF DESCRIPTION OF THE DRAWINGS

Now, several embodiments of the invention will be described using drawings, in which:

FIG. 3 is an axial cutaway view of a first element of the connecting device of FIG. 1;

FIG. 4 is an end view of the first element of FIG. 3, from its distal end;

DETAILED DESCRIPTION OF THE PREFERRED EMBODIMENTS

Figure 1:
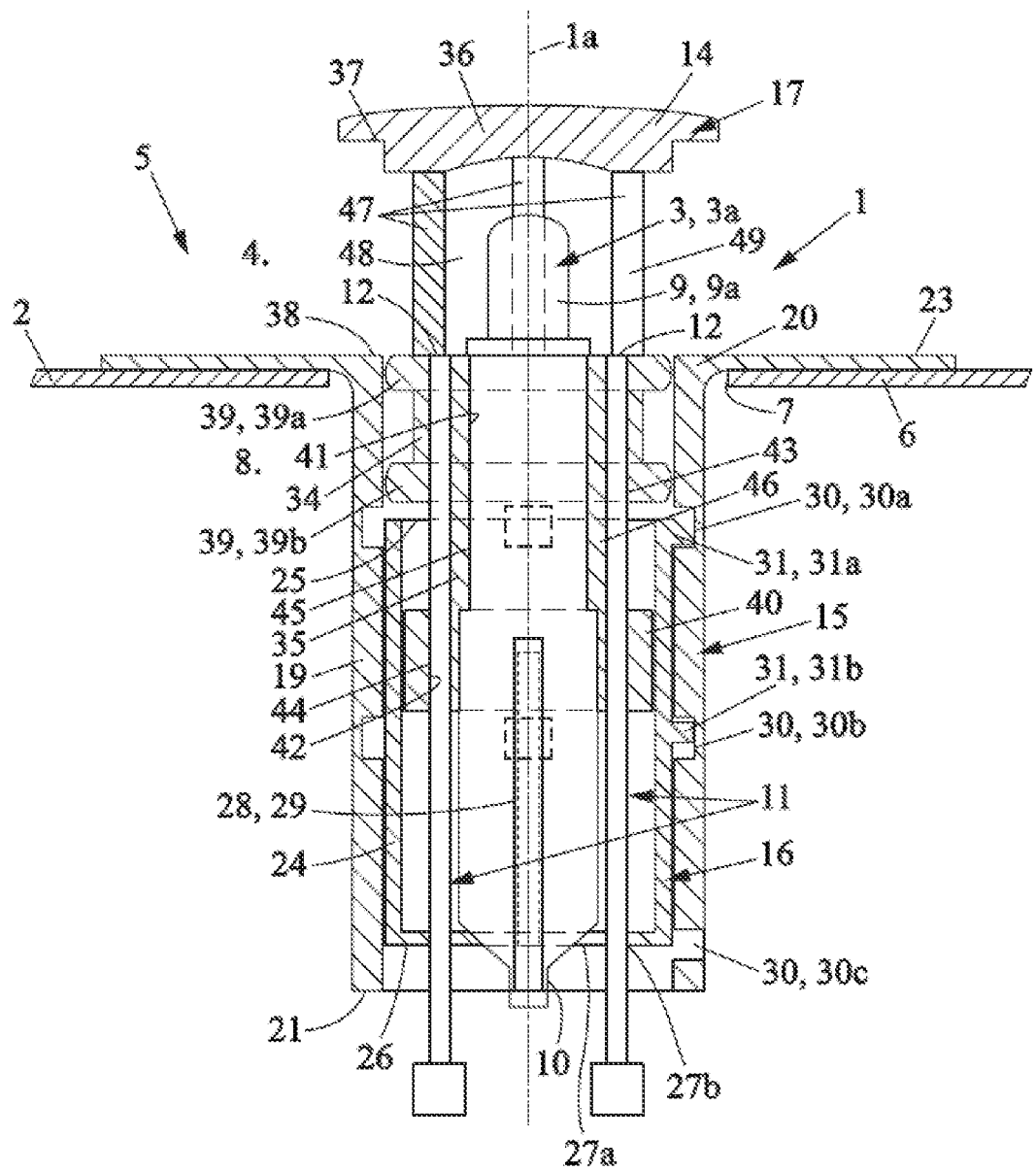
FIG. 1 is an axial cutaway view of a connecting device, whereby the accessory that is shown diagrammatically is a probe here, the connecting device and the probe are in a first distal state that corresponds to a storage and/or calibration situation, a functional part that is a drainage and calibration tube here is associated with the accessory, and the connecting device is mounted on the receptacle whose peripheral wall is only shown partially.

A device 1 is intended for the connection to a receptacle 2 of an accessory 3 that can be put into communication with the inside 4 of the receptacle 2. "Connecting" is defined as the fact that originally, the receptacle 2 and the accessory 3 are totally distinct and separate and that using the device 1, the accessory 3 is attached and connected to the receptacle and that a functional link can be established between the receptacle 2 and its contents, and the accessory 3. "First unit" refers to the unit that comprises the connecting device 1 and the accessory 3, and "second unit" refers to the unit that comprises the first unit 1, 3 and the receptacle 2.

Conventionally, the unit that comprises the receptacle 2, the connecting device 1, and the accessory 3 is referred to by the name of "functional container" 5. This functional container 5 is intended for storage and/or treatment of a biopharmaceutical product, referred to below as contents.

According to the embodiments that are being considered, the receptacle 2 is rigid and can be reused, or it is flexible and disposable, such as a pocket such as a so-called 2D pocket or a so-called 3D pocket, as it was defined above.

In one embodiment, such a 3D pocket is generally parallelepipedic in shape, in particular cubic or essentially cubic, having a peripheral wall 6, forming at least the bottom and the lateral part, and most often the upper part, in such a way that the receptacle 2 is of the closed type, and one or more ports that are suitable for the purpose, arranged on the wall 6. In one embodiment that corresponds to a high volume that exceeds 50 l and can reach 3,000 l, the receptacle 2 can be folded.

With such a flexible receptacle 2, it is provided that the container 5 also includes rigid means for holding from the outside. These means, whose existence is known in the art, are not shown. It may be in particular a metal tank that may or may not have solid walls.

The wall 6 of the receptacle 2 is provided with an opening 7 that is intended for mounting, crosswise relative to the wall 6, the connecting device 1 and the accessory 3, so that the latter can be put into communication with the inside 4 of the receptacle 2 and in particular can be brought into contact with the contents of the receptacle 2, whereas the accessory 3 is located at least substantially in the outside 8 of the receptacle 2.

What was just described in the case of a 3D pocket can be transposed in the case of a 2D pocket and to the case of a rigid receptacle 2.

The device 1, such as most often the accessory 3, has a longitudinal axis 1a that is placed at least approximately perpendicular to the wall 6.

The inside 4 of the receptacle 2 is conventionally defined as the inside zone in the receptacle 2, delimited by the jacket of the wall 6, located on the side where the largest part of the contents is located. The outside 8 of the receptacle 2 is defined as the zone that is located on the other side of the jacket of the wall 6.

The rigid means for holding the receptacle 2 from the outside, when they are provided, comprise a passageway for the connecting device 1, located opposite or approximately opposite the opening 7.

The term "accessory" does not mean that the object 3 that it refers to would be secondary or simply optional, but that this object 3 is complementary and depends heavily on the receptacle 2 and the contents of the latter by having a function accompanying that of the receptacle 2.

Within the scope of the invention, the accessory 3 is preferably disposable, just like the connecting device 1.

According to a first embodiment (FIGS. 1, 2 and 8), the accessory 3 is a probe 3a that comprises an active proximal part 9a that can measure, detect, monitor, record (subsequently measure) one or more useful parameters that relate to the contents, such as in particular pressure, pH, temperature, colorimetry, and conductimetry.

Figure 2:
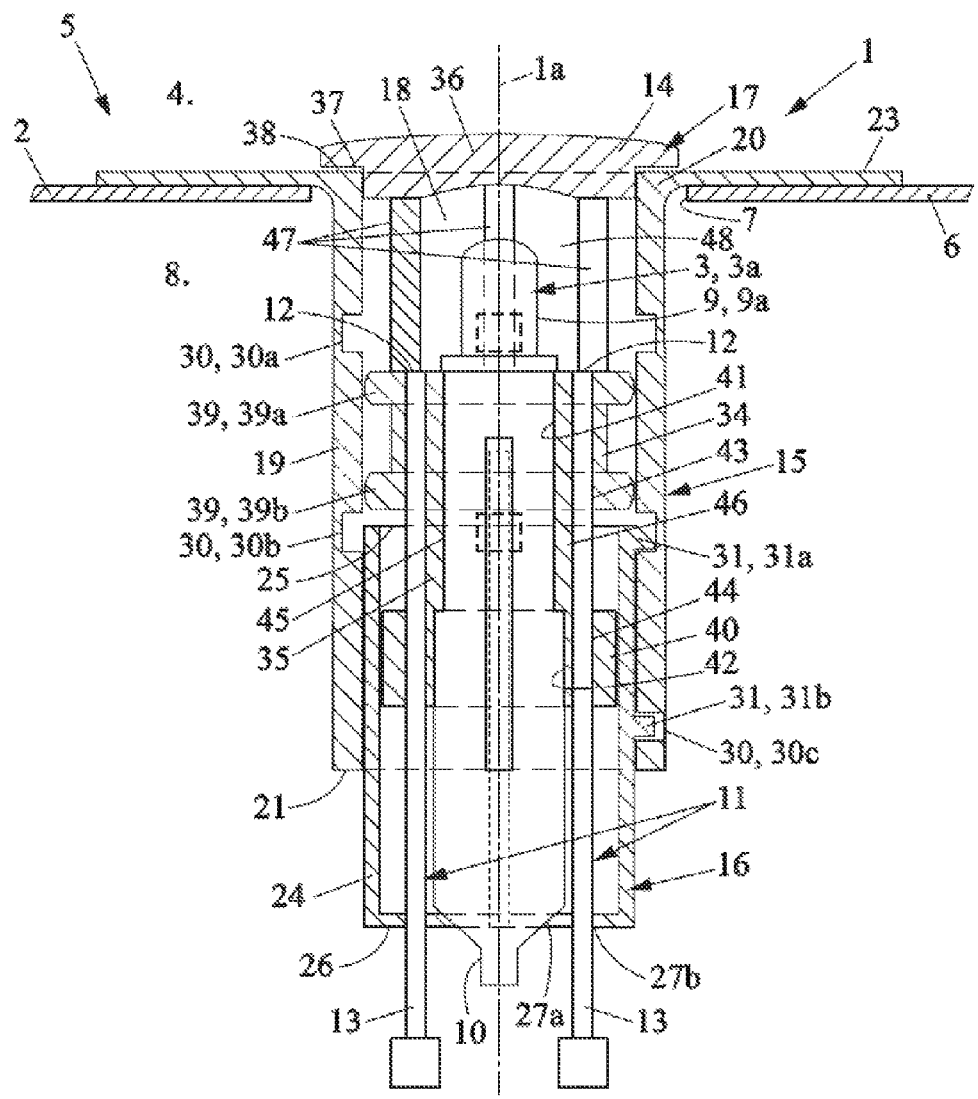
FIG. 2 is a view of the connecting device of FIG. 1 when the connecting device, the probe, and the drainage and calibration tube are in a second proximal state that corresponds to a situation for using the probe.

The active part 9a of the probe 3a is able, when necessary, to be put into communication with the inside 4 of the receptacle 2, and more especially to be brought into contact with the contents of the receptacle 2 so as to be able to play its measuring role. In this case, it is provided, in an embodiment that is shown in FIG. 2, that the active proximal part 9a is able to be introduced into the inside 4 of the receptacle 2 by passing through the opening 7 of the wall 6 to go beyond the latter so as to be in close contact with the contents, in a zone where the latter is homogeneous, or at least homogeneous enough regarding the parameter in question, with the remainder of the contents of the receptacle 2. The opening 7 is then preferably located on or toward the bottom of the receptacle 2, i.e., so as to be found at a lower level than the level of the contents of the receptacle 2, even when the content amount is low and the level is close to the bottom of the receptacle 2.

In another embodiment, not shown, the active proximal part 9a of the probe 3a is not able, strictly speaking, to be introduced into the inside 4 of the receptacle 2 but to be brought below the wall 6 and close to the opening 7 without, however, passing through it, so as to be in communication with the inside 4 of the receptacle 2.

In another embodiment, not shown, the active proximal part 9a of the probe 3a is able to be brought into the opening 7, in the plane of the wall 6, in such a way as to be in communication with the inside 4 of the receptacle 2.

In these various embodiments, situations and positions, the active proximal part 9a of the probe 3a (and the probe 3a itself) is suited to be inserted into the receptacle 2 or into the inside 4 of the receptacle 2.

In other embodiments that can be combined with the preceding ones, not one but several probes 3a are provided either for several parameters or at different locations, in particular in terms of height, of the receptacle 2.

Figure 9:
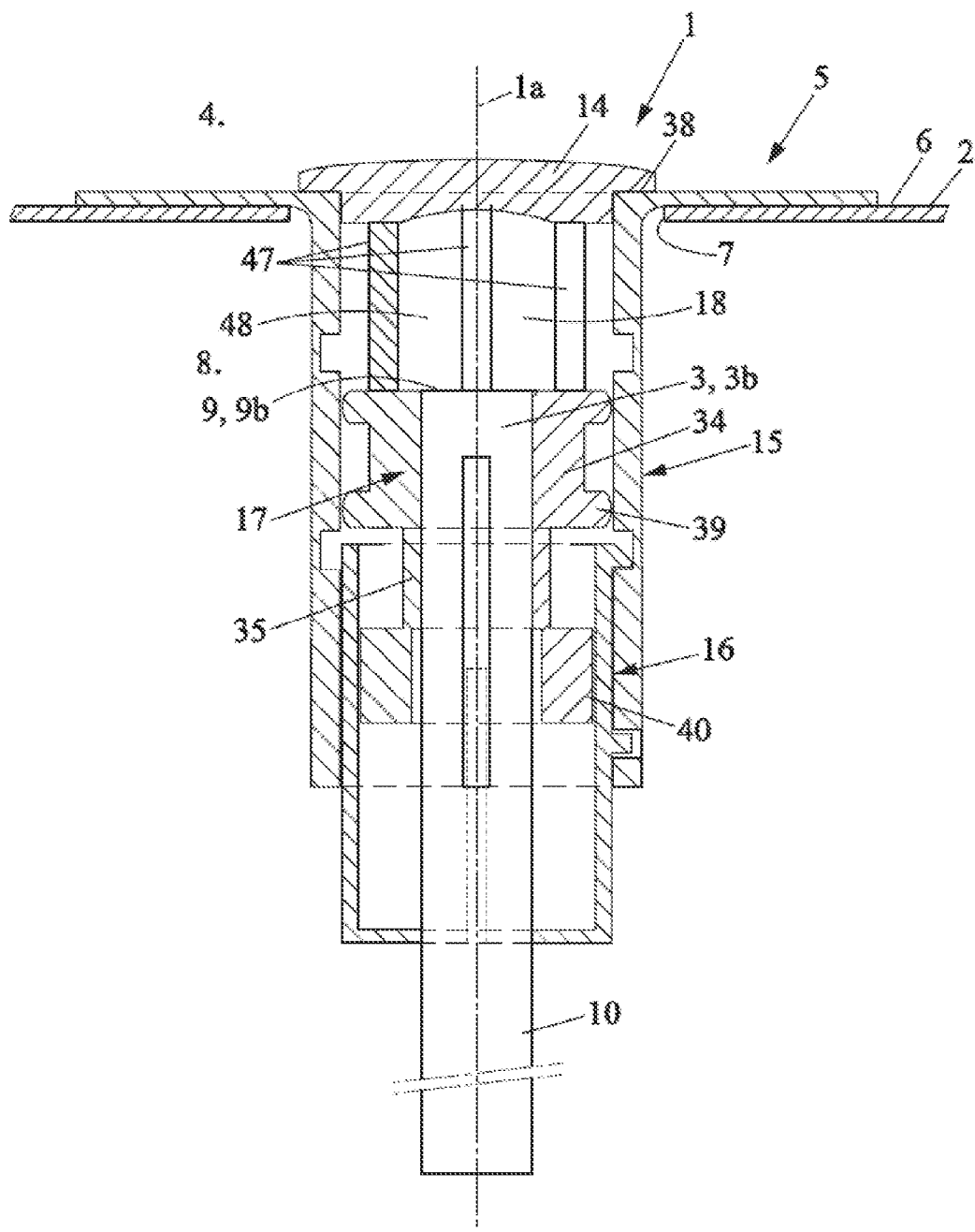
FIGS. 9 and 10 are two analogous views respectively to FIGS. 1 and 2, whereby the accessory here is a filling and/or drainage tube.
Figure 10:
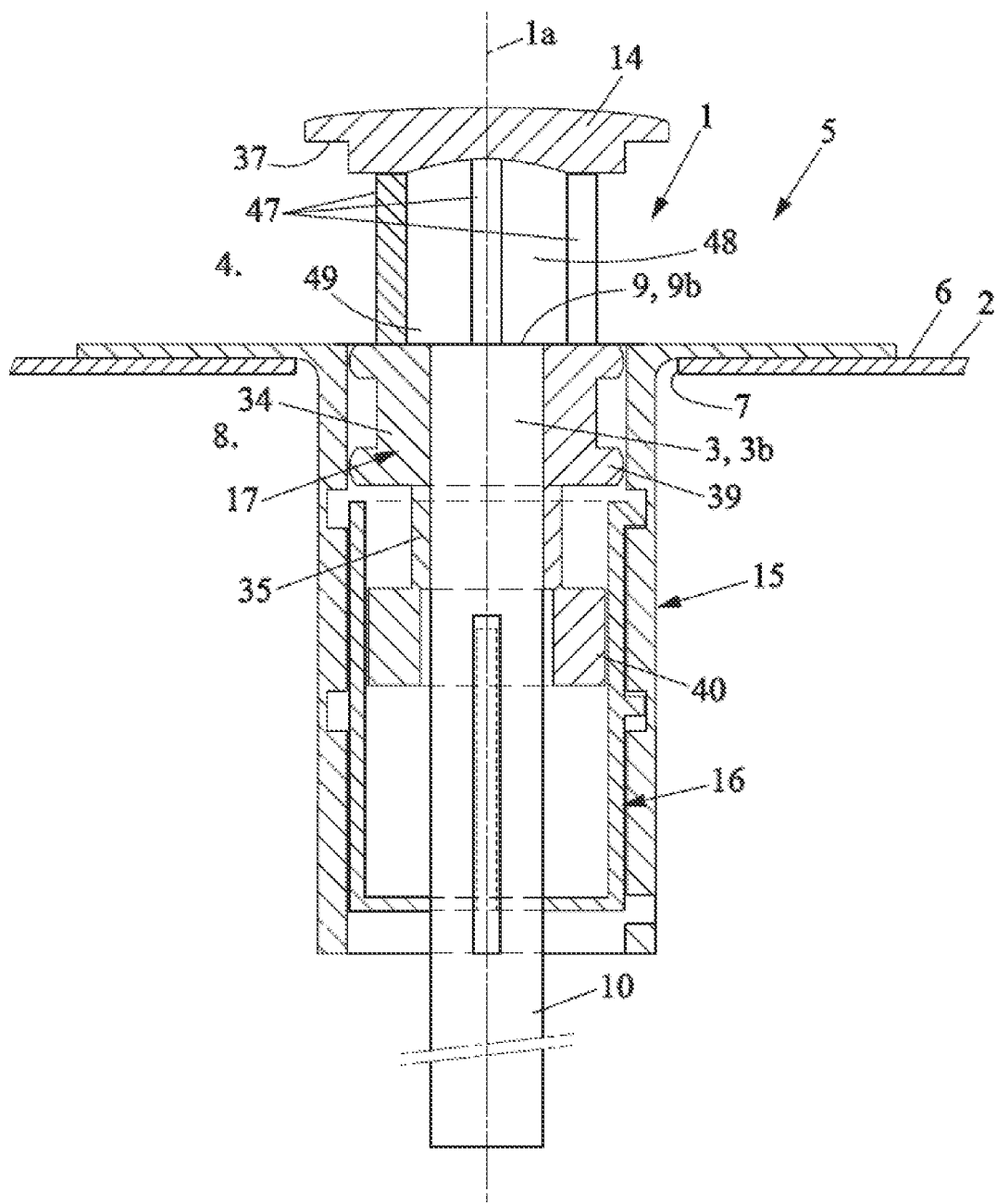

According to a second embodiment (FIGS. 9 and 10), the accessory 3 is an intake tube 3b and/or a drainage tube 3b for the contents of the receptacle 2 or one or more components of the latter. This tube 3b comprises an active proximal part 9b toward the receptacle 2 that consists of an intake opening if the tube is, or acts like, an intake tube, or consists of a drainage opening if the tube is, or acts like, a drainage tube, whereby this opening is conventionally located at the free end of the tube 3b.

The active proximal part 9b of the tube 3b is able, when necessary, to be put into communication with the inside 4 of the receptacle 2 so as to be able to play its intake and/or drainage role(s). In line with the active proximal part 9a of the probe 3a, the active proximal part 9b of the tube 3b is then able either to be taken in either into the opening 7, in the plane of the wall 6 (FIG. 10), or to be introduced into the inside 4 of the receptacle 2 by passing through the opening 7 of the wall 6 (not shown), or to be taken in below the wall 6 and close to the opening 7 without, however, passing through it (not shown). These various embodiments, situations and positions correspond to what has been defined as the insertion of the active proximal part 9b into the receptacle 2 or into the inside 4 of the receptacle 2.

When the accessory 3 is an intake tube 3b and/or a drainage tube 3b, the opening 7 is located relative to the bottom of the receptacle 2 at the height that is appropriate for the purpose of the tube 3b, either at a level that is close to the bottom of the receptacle 2 or, in contrast, at a level that is more or less removed from the bottom.

In line with the probe 3a, several tubes 3b can be provided either for different components or at different locations, in particular in terms of height, of the receptacle 2. In contrast, the same tube can have several functions: intake, drainage and/or several different components.

According to other embodiments, the accessory 3 is intended for a function other than measurement, intake or drainage. Instead of being rigid, this accessory 3 can be more or less deformable. It may optionally involve a functional accessory that is useful for the contents of the receptacle 2, for example a mixing means.

In a general way, the accessory 3 comprises an outside jacket that is more or less complex in shape, elongated, and in particular for a revolution on a circular base. Its proximal end active part is referenced 9, and its distal end part is referenced 10. Means such as an electrical conductor, tube, . . . can be associated with this distal end part 10.

In the embodiment that is shown, the accessory 3 is arranged centrally relative to the axis 1a.

According to the embodiments, at least one other functional part 11, placed beside or close to the accessory 3 and extending along axis 1a, is functionally associated with the accessory 3 itself by being eccentric relative to it. Such a functional part 11 also comprises an outside jacket, elongated, and in particular for a revolution on a circular base. In the embodiment shown, the functional part 11 takes up a transverse space that is considerably smaller than that of the accessory 3.

Such a functional part 11 is, in one embodiment, one or more intake and/or drainage tubes associated with a probe 3a so as to ensure in particular its calibration, as will be described below. In such a case, the tube 11 comprises an open proximal end part 12 and an open distal end part 13 that can come, in one embodiment, in the form of a Luer-type connection end fitting or a filter or the like.

In a specific embodiment, such as the one that corresponds to the case where the accessory 3 is a pH probe 3a, the functional part 11 preferably comprises at least two tubes, one an intake tube, and, if necessary, a calibration tube, and the other a drainage tube, and, if necessary, a rinsing tube.

The term "proximal" conventionally refers to what is, in a relative way, close, or closer, to a receptacle 2, in particular its interior 4. Conversely, the term "distal" refers to what is, in a relative way, removed, or further removed, from the receptacle 2, in particular from its interior 4. These terms are used to reference the constituent parts of the connecting device 1, the accessory 3, and the functional part 11. It is understood, however, that the connecting device 1 or the accessory 3 or the functional part 11 can be considered by itself, independently of the receptacle 2, before mounting on the latter. These terms are also used to reference the location of the constituent parts of the device 1 of the accessory 3 and of the functional part 11 relative to the receptacle 2 or to reference their position relative to the latter, if this position is not stationary. Finally, these terms are conventionally used to distinguish the two states in which the connecting device 1, the accessory 3, and the functional part 11 can be found.

The connecting device 1, the accessory 3, and in particular its active proximal part that is generally referenced 9, the functional part 11, and in particular its distal end part 13, can be found in one of two possible states described below, corresponding to two possible relative positions relative to the receptacle 2, to two states, functions or possibilities of action. These states are understood when the connecting device 1, the accessory 3, and the functional part 11 are mounted on the receptacle 2. As above, it is understood, however, that the connecting device 1 or the accessory 3 or the functional part 11 can be considered by itself, independently of the receptacle 2, before mounting on the latter.

The two possible states are a first state termed distal and a second state termed proximal. The terms "first" and "second" express the idea that at the beginning, one is in the distal state.

In the first distal state, the active proximal part 9 of the accessory 3, if necessary the proximal end part 12 of the functional part 11, is totally separated, in an airtight manner, from the inside 4 of the receptacle 2 by a top 14 that forms a barrier, forming part of the connecting device 1.

In the second proximal state, the active proximal part 9 of the accessory 3, if necessary the proximal end part 12 of the functional part 11, is in communication with the inside 4 and inserted into the receptacle 2. The top 14 then forms a protection of the active proximal part 9, and, if necessary, the proximal end part 12 of the functional part 11.

In the case where the accessory 3 is a probe 3a, the first distal state is typically the one that corresponds to storage or to calibration, while the second proximal state is typically the one of the measurement, for the contents of the receptacle 2, of the parameter that corresponds to the probe 3a that is used.

In the case where the accessory 3 is a tube 3b, the first distal state is typically the one that corresponds to the storage or to the disuse of the filling or drainage function of the tube 3b, while the second proximal state is that of the filling or drainage function of the tube 3b.

The connecting device 1 comprises a first element 15, a second element 16, and a third element 17, separate, assembled together and functionally working with the accessory 3, and, if necessary, the functional part 11. The connecting device 1 also comprises a chamber 18.

The first element 15 has several functions:
It ensures the rigid attachment of the connecting device 1 to the receptacle 2.
It defines a channel between the inside 4 and the outside 8 of the receptacle 2.
For the second element 16, it is used as a support and as an axial translation guide along the axis 1a, over a given course C whose two ends of travel respectively correspond to the first distal state and the second proximal state.
It helps to serve as a guide for the third element 17.
It helps to delimit the chamber 18.

The second element 16 also has several functions:
It serves as a support to the third element 17, which is attached rigidly to it.
It forms a moving, axially sliding element along the axis 1a on the course C whose two ends of travel correspond respectively to the first distal state and the second proximal state.

The third element 17, to which the top 14 belongs, also has several functions:
It serves as a support to the accessory 3, and, if necessary, to the functional part 11, which is (are) attached rigidly to it.
It forms a moving, axially sliding element along the axis 1a on the course C whose two ends of travel correspond respectively to the first distal state and the second proximal state.
In the first distal state, it ensures, using the top 14, the airtight closing of the opening 7 by forming a barrier that prevents access to the inside 4 of the receptacle 2 and the communication between the accessory 3 and, if necessary, the functional part 11, with the inside 4 of the receptacle 2.
In the second proximal state, it ensures, using the top 14, protection of the active proximal part 9 of the accessory 3 and, if necessary, the proximal end part 12 of the functional part 11, primarily when one and/or the other is introduced, strictly speaking, into the inside 4 of the receptacle 2.
It also helps to delimit the chamber 18.

Figure 5:
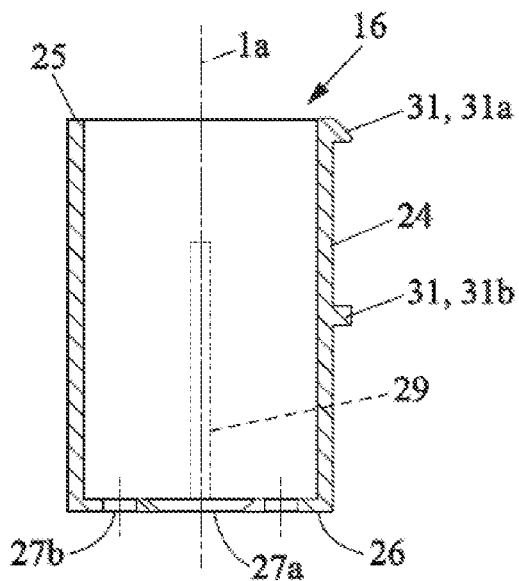
FIG. 5 is an axial cutaway view of a second element of the connecting device of FIG. 1 that shows the lugs forming part of the end-of-travel locking means.
Figure 6:
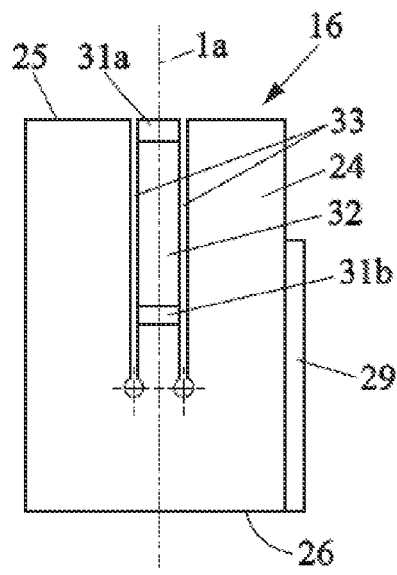
FIG. 6 is an elevation view of the second element of FIG. 5 that shows an elastic foot.
Figure 7:
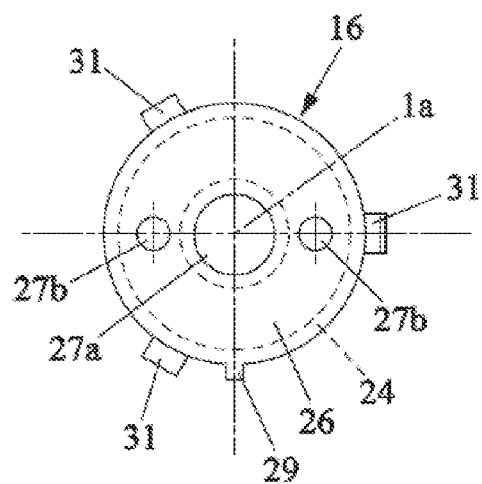
FIG. 7 is an end view of the second element of FIG. 5 from its distal end.

The first element 15 is now described more especially with reference to FIGS. 3 and 4, and the second element 16 is now described more especially with reference to FIGS. 5, 6 and 7.

The first element 15, rigid and one-piece, comprises a tubular wall 19, cylindrical with a circular square base, extending over a certain axial length L1. This tubular wall 19 is open at its two ends, respectively proximal 20 and distal 21, so as to allow the passage, toward the proximal end 20, of the third element 17, if necessary the active proximal part 9 of the accessory 3, and the proximal end part 12 of the functional part 11, and, toward the distal end 21, the second element 16, the accessory 3, and the functional part 11, in particular from the side of their distal parts 10, 13.

The first element 15 and its tubular wall 19 form a channel 22 for the contents of the receptacle 2 from the inside 4.

At the proximal end 20, the first element 15 comprises a flange 23 for attachment to the receptacle 2 in the form of a transverse annular collar, directed laterally toward the outside. The outside diameter of the tubular wall 19 corresponds to the diameter of the opening 7 in such a way that the first element 15 can adjust in the opening 7. The flange 23, located in the extension of the wall 6 and with an adequate radial expanse, is attached to the latter around the opening 7 in a rigid and airtight manner, for example by ultrasonic welding, gluing or another analogous manner.

The first element 15 extends along the axis 1a, toward the outside 8 of the receptacle 2.

The second element 16, rigid and one-piece, comprises a tubular wall 24, cylindrical with a circular base, extending over a certain axial length L2 that is slightly smaller than the length L1 in the embodiment that is shown in the figures.

This tubular wall 24 is open at its proximal end 25 by thus being able to allow the passage of the third element 17, the accessory 3, and, if necessary, the functional part 11. The tubular wall 24 is open at its distal end 26 by thus being able to allow the passage of the accessory 3 and, if necessary, of the functional part 11, in particular toward or beside their distal parts 10, 13. According to the embodiments, the distal end 26 is totally open, or it comprises a transverse wall that is provided with an opening 27a for the distal part 10 of the accessory 3 and, if necessary, an opening 27b for the distal part 13 of the functional part 11. According to other embodiments, a larger number of openings, adapted to the number of accessories 3 and functional parts 11, is provided.

The outside diameter of the tubular wall 24 of the second element 16 corresponds to the necessary play close to the inside diameter of the tubular wall 19 of the first element 15 in such a way that the first element 15 forms a support and an axial movement guide along the axis 1a on the course C for the second element 16.

The inside surface of the tubular wall 19 and the outside surface of the tubular wall 24 comprise a combination of axial groove 28 and radial projection 29 toward the outside. The radial projection 29 can be housed adjusted in, and can slide along, the axial groove 28, over an axial length that is at least equal to the course C. The combination of axial groove 28 and radial projection 29 forms a guide that defines and maintains the relative angular orientation between the first element 15 and the second element 16.

In the embodiment shown, the groove 28 is arranged in the first element 15 and extends from its distal end 21. The radial and axial projection 29 is arranged on the second element 16 and extends from its distal end 24. This structural arrangement makes possible the mounting of the second element 16 on the first element 15 by relative axial sliding of the second element 16 in the first element 15 from its distal end 21 toward its proximal end 20.

The inside surface of the tubular wall 19 and the outside surface of the tubular wall 24 comprise a combination of retractable slot(s) 30 and lug(s) 31, arranged radially and able to work together. The combination of slot(s) 30 and lug(s) 31 forms removable means 30, 31 for locking the end of travel of axial movement along the axis 1a of the second element 16 on and relative to the first element 15 on the course C.

To make possible the slot 30/lug 31 cooperation, it is provided that a lug 31 is arranged so as to be stressed elastically radially toward the outside and toward the bottom of an opposing slot 30 so as to be housed there. Conversely, to make possible the slot 30/lug 31 autonomy, it is provided that a lug 31 is arranged so as to be able to be retracted from a slot with which it was working and thus to withdraw elastically radially toward the inside to be able then to slide on the surface opposite the element that carries the slot(s) 30, once the lug 31 is located outside and away from a slot 30.

These axial movement end-of-travel locking means with slot(s) 30 and lug(s) 31 can be the object of several embodiments.

In the simplest embodiment, two slots 30 and one lug 31, or, conversely, one slot 30 and two lugs 31 are provided. If the first element 15 accommodates a lug 31, the second element 16 accommodates a slot 30. Conversely, if the first element 15 accommodates a slot 30, the second element 16 accommodates a lug 31. Slot(s) 30 and lug(s) 31 are positioned angularly so as to be able to cooperate, taking into account the guide 28, 29. Those of the slots 30 or lugs 31 that are two in number are, on the same generatrix, separated along the axis 1a by a distance C that corresponds to the translational travel. In this embodiment, each of the two translational ends of travel is defined by the cooperation of a lug 31 in a slot 30.

In another embodiment, it is provided that each slot 30 and each lug 31 is not single, but double, triple, quadruple . . . in the same transverse plane relative to the axis 1a. In this case, these multiple slots 30 and lugs 31 are preferably also distributed angularly around the axis 1a. In this embodiment, each of the two ends of travel is defined by the cooperation of several lugs 31 in several slots 30.

In another embodiment, it is provided that a slot 30 and/or a lug 31 is not single but double, triple, quadruple, . . . separated judiciously along the axis 1a. In this embodiment, each of the two ends of travel is defined by the cooperation of several lugs 31 in several slots 30.

These embodiments can be combined with one another, whereby each slot 30 and each lug 31 is not single, but double, triple, quadruple, . . . in the same transverse plane relative to the axis 1a and whereby a slot 30 and/or a lug 31 is not single, but double, triple, quadruple, . . . along the axis 1a. Such a combination makes it possible to reduce the risk of slot 30/lug 31 dismantling and therefore the preservation of end-of-travel positions in the absence of ill-timed external stress.

Such a combination corresponds to the embodiment that is shown in FIGS. 3 to 7. According to this embodiment, the slots 30 are arranged on the first element 15, and the lugs 31 are arranged on the second element 16. On the one hand, each slot 30 and each lug 31 is triple with an angular separation of 120°. On the other hand, three such slots 30 that are judiciously separated along the axis 1a and two such lugs 31, also separated along the axis 1a, are provided.

According to this embodiment, more specifically, three proximal slots 30a, three intermediate slots 30b, and three distal slots 30c are first of all provided on the inside surface of the tubular wall 19 of the first element 15. The three proximal slots 30a are located toward, but separated from, the proximal end 20. The three distal slots 30c are located in the immediate proximity of the distal end 21. The three intermediate slots 30b are also separated axially from the proximal slots 30 and distal slots 30c. Three proximal lugs 31a and three distal lugs 31b are then provided on the outside surface of the tubular wall 24 of the second element 16. The three proximal lugs 31a are located in the immediate proximity of the proximal end 22. The three distal lugs 31b are essentially also separated axially from the proximal end 23 and the distal end 24.

In the first distal state, the three proximal lugs 31a work with the three intermediate slots 30b, and the three distal slugs 31b work with the three distal slots 30c.

In the second proximal state, the three proximal lugs 31a work with the three proximal slots 30a, and the three distal lugs 31b work with the three intermediate slots 30b.

Consequently, in the first distal state, the second element 16 is laterally opposite the first element 15, without being opposite a part of the first element 15 that is adjacent to its proximal end 20, a part of the second element 16 projecting from the distal end 21 of the first element 15.

In the second proximal state, the second element 16 is laterally completely opposite the first element 15 toward its distal end 21, without being opposite a shorter part axially from the first element 15 that is adjacent to its proximal end 20.

Regarding the slot/lug cooperation/autonomy, it is provided, in the embodiment shown, that two lugs 31a, 31b, separated along the axis 1a, are carried by a foot 32, in axial direction and elastically deformable in its unit, formed by a part of the tubular wall 24 that is adjacent to one end, distal in the embodiment shown, but elsewhere separated from the rest of the tubular wall 24 by a slit 33 (with or without removal of material). In the embodiment shown, the proximal end of the foot 24 is combined with the proximal end 25 of the second element 16. As for its distal end, it is located, along the axis 1a, between the distal lug 31b and the distal end 26 of the second element 16. By this structural arrangement, the same foot 32 can carry the two lugs 31a, 31b, whereby the distal lug 31b is sufficiently removed from the connection between the foot 32 and the tubular wall 24 to be able to be retracted as a result of the deformation of the foot.

Advantageously, the first and second elements 15 and 16 are made of polyethylene or polypropylene.

Figure 8:
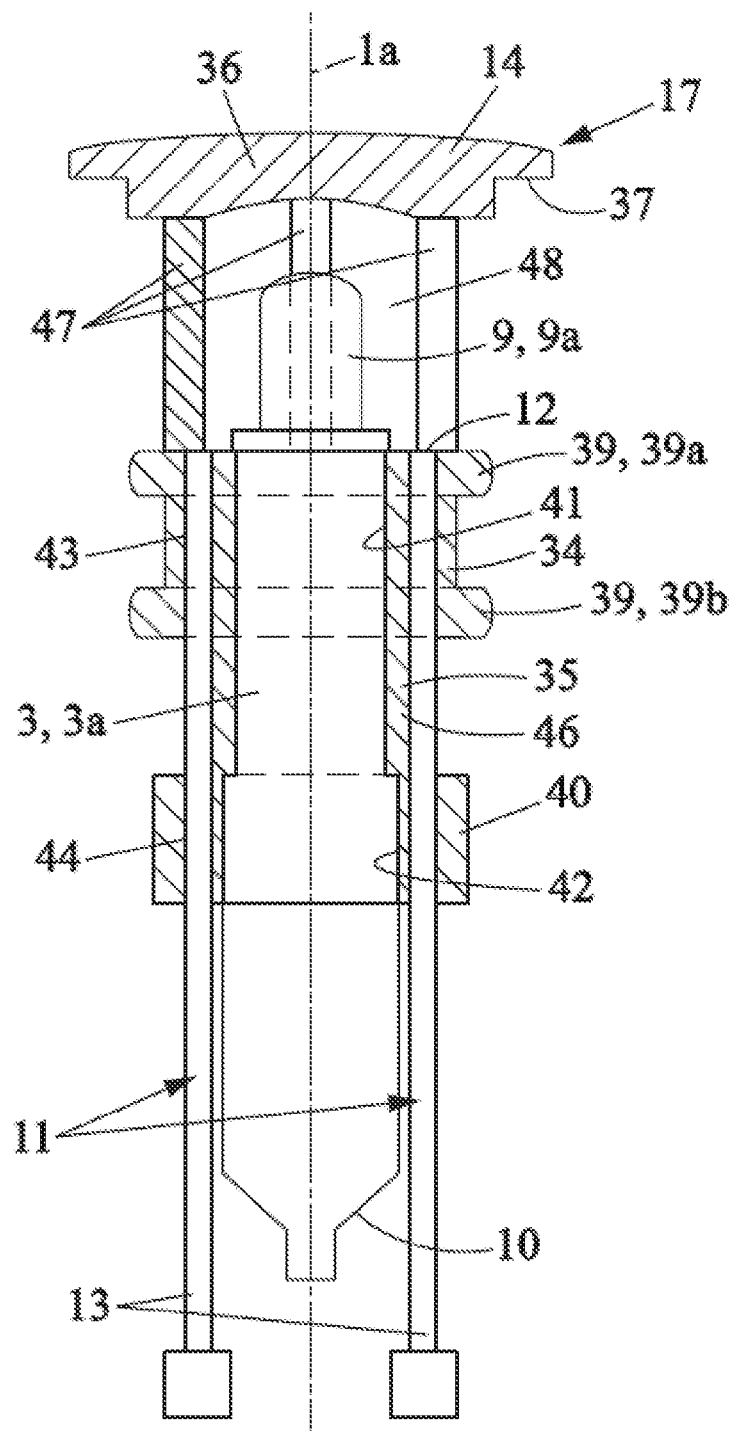
FIG. 8 is an axial cutaway view of a third element of the connecting device of FIG. 1, also showing the accessory, namely the probe, and the associated functional part, namely the drainage and calibration tube.

The third element 17 is now described more especially with reference to FIG. 8.

The third element 17, in several pieces, for a revolution around the axis 1a, comprises the top 14, a base 34, and a body 35, forming a rigid unit.

The top 14 has two functions:

In the first distal state, the top 14 closes the opening 7 and the first element 15 in an airtight manner by forming a barrier that prevents access to the inside 4 of the receptacle 2 and the communication between the accessory 3, and, if necessary, to the functional part 11, with the inside 4 of the receptacle 2.

In the second proximal state, the top 14 helps to protect the active proximal part 9, and, if necessary, the proximal end part 12, primarily when one and/or the other is introduced, strictly speaking, into the inside 4 of the receptacle 2 by having passed through the opening 7. Actually, it is possible, for example, that there are agglomerates in the contents or that an element (tube, shaft, propeller, distributor . . . ) has been introduced into the receptacle 2, where said element is able in some cases to damage the active proximal part 9, if necessary the proximal end part 12, introduced into the inside 4 of the receptacle 2.

The top 14 comes in the general form of a full transverse wall 36 that forms a sort of cover or flap, which is able to work with the opening 7 to close it in an airtight way when necessary and to be separated from it by axial sliding to open it.

The peripheral edge of the top 14 forms an offset 37 that can work with and take up, in an airtight manner, the support and holding seat formed by the proximal end 20 and the adjacent part 38 of the flange 23.

The top 14 has an overall elastic deformability that makes it possible, on the one hand, to ensure the airtight cooperation with the support and holding seat, and, on the other hand, to be deformed in the direction of a reduction of its outside diameter, so as to be able to be—for the mounting—inserted into the first element 15 by its distal end 21.

In the first distal state, the top 14 rests on the seat that the first element 15 forms by closing the opening 7 in an airtight manner. It is then located if not in, at least close to, the plane of the opening 7 and the wall 6. In the second proximal state, the top 14 is introduced into the inside 4 of the receptacle 2 by passing through the opening 7 of the wall 6 to go beyond the latter.

The base 34 has several functions:

It serves as a support to the accessory 3, and optionally to the functional part 11, which is (are) attached rigidly to it.

In combination with the first element 15, it ensures the sliding guide, with sealing, of the third element 17 on and relative to the first element 15.

It helps to delimit the chamber 18.

The base 34 first comprises, in its proximal end part, a first ring 39, capable of being able to slide axially, with sealing, by its outside surface, on and along the inside surface of the tubular wall 19 of the first element 15. For this purpose, the first guide ring 39 has an outside nominal diameter that corresponds to the inside diameter of the tubular wall 19 so that it has sliding contact and sealing between the outside surface of the first ring and the inside surface of the tubular wall 19 of the first element 15.

In the embodiment that is shown, two first rings 39$a$ and 39$b$ are provided that are separated from one another along the axis 1$a$, which makes it possible to combine good guiding by a sufficient scope, good sliding, and good sealing at the same time.

Secondly, the base 34 comprises, at its distal end part, a second ring 40, able to be attached rigidly by its outside surface, on and against the inside surface of the tubular wall 24 of the second element 16, in or in the vicinity of its median part between its proximal end 25 and its distal end 26. Thus, the first ring 39 is located outside of the second element 16, but in the immediate proximity of its proximal end 25. The second ring 40 is therefore sized and positioned for the purpose of obtaining these results.

The inside surfaces 41 and 42, respectively, of the first ring 39 and the second ring 40 are able to make possible the rigid attachment, with an overall sealing, of the accessory 3 by its outside surface. The axial position of the accessory 3 relative to the base 34 is such that the active proximal part 9 projects proximally from the first ring 39 or is flush with its proximal end. The first case is well suited when the accessory 3 is a probe 3$a$ while the second case is well suited when the accessory 3 is an intake or drainage tube 3$b$. In all of the cases, the inside surfaces 41 and 42 are sized for the purpose of making this rigid and overall airtight attachment possible. This rigid attachment is implemented by, for example, gluing.

If necessary, the first ring 39 and the second ring 40 comprise at least two channels in alignment 43 and 44, able to make possible the mounting on the inside as well as the rigid attachment, with sealing, of the functional part 11 that is placed beside or close to the accessory 3 by being eccentric relative to the axis 1$a$. The axial position of the functional part 11 relative to the base 34 is such that the proximal end part 12 is flush with the proximal end of the first ring 39 or projects proximally from the latter. The first case is well suited when the functional part 11 is an intake or drainage tube, while the second case is well suited when the functional part 11 is, for example, a measuring element. The rigid attachment of the functional part 11 is implemented by, for example, gluing.

The body 35 comprises a connecting part 46 that connects the first and the second rings 39 and 40 and that comprises an axial, through bore 45 into which the accessory 3 is inserted. If necessary, the accessory 3 is also attached to the surface of this bore 45, and therefore to the connecting part 46.

In the embodiment that is shown, this connecting part 46 has an outside diameter that is smaller than the outside diameter of the first and second rings 39 and 40. This arrangement makes it possible for the functional part 11, if it exists, to be placed outside of the connecting part 46.

If necessary, the connecting part 46 comprises at least one channel or a slot that is aligned with the channels 43 and 44.

The body 35 also comprises one or more carrying elements 47, rigidly connecting the top 14 and the base 34, namely the proximal end of the first ring 39. The (or these) carrying element(s) 47 is (are) rigid enough to ensure effective holding of the top 14. In contrast, this (or these) carrying element(s) 47 is (are) arranged to make possible a passage through the contents of the receptacle 2 and/or a fluid that is drawn in or drained through a functional part that is provided for this purpose, for example for the calibration of the probe 3$a$.

The carrying elements 47 can come in the form of rods that extend axially, arranging passageways 48 between them, or in the form of a sleeve that is provided with such passageways 48.

In the embodiment that is more especially considered, the third element 17, with the exception of the carrying elements 47, is carried out in a single piece by casting, in a material that ensures good sealing and that has a certain elastic deformability as already indicated for the top 14, and a certain sliding quality, such as silicone. Regarding the carrying elements 47, they are advantageously made of stainless steel or any other material that has the desired rigidity. In other embodiments, the third element is made of several pieces that are assembled in a different way.

The third element 17 extends over a certain axial length L3, slightly smaller than L1.

The accessory 3 extends over a certain axial length L4, in this case slightly greater than L1 and L3.

The axial length of the carrying elements 47 is suitable for making possible the housing of the active proximal part 9, when it projects from the proximal end of the first ring 39, and, in the second proximal state, the passageway without hindrance from the contents of the receptacle 2 to the chamber 18 where a probe 3a is located, or fluid that comes from or goes toward the tube 3b.

In the first distal state, the third element 17 is completely housed within the first element 15 with the exception of the top 14. In the second proximal state, the top 14 and the carrying elements 47 of the third element 17 are located outside of the first element 15, whereby the first ring 39 is located in the opening 7. In this second proximal state, the first ring 39, the second ring 40, and the connecting part 46 are completely housed within the first element 15, whereby the second ring 40 is located toward the distal end 21 of the first element 15.

The relative position of the third element 17 relative to the second 16 is stationary. The second ring 40 and the connecting part 46 are completely located within the second element 16. The first ring 39, the carrying elements 47, and the top 14 are completely located outside of the second element 16.

In the first distal state, the chamber 18 is closed in an airtight manner, and it is delimited by the first element 15 and the third element 17, if the active proximal part 9 of the accessory 3—which, housed inside (the case of the active proximal part 9a) or placed on the periphery (the case of the active proximal part 9b) of the chamber 18, helps in a certain manner to delimit it—is set aside.

More specifically, in the first place, the chamber 18 is limited at its two axial end parts, on the one hand, by the distal transverse surface of the wall 36 that forms the top 14, which closes the opening 7, and, on the other hand, by the transverse surface of the proximal end of the first ring 39. In the second place, the chamber 18 is limited at its periphery by the inside surface of the tubular wall 19 of the first element 15.

The sealing of the chamber 18, in the first distal state, is ensured by the sealing that is provided between the top 14 and its seat that belongs to the first element 15, between the first ring 39 and the inside surface of the tubular wall 19, between the accessory 3 and the third element 17, and if necessary between the first ring 39 and the functional part 11.

The chamber 18 is such that the active proximal part 9 is either housed inside (the case of the active proximal part 9a of a probe 3a), or placed on the periphery (the case of the active proximal part 9b of a tube 3b), such that the active proximal part 9 is in contact or in communication with the chamber 18 or the fluid that it contains.

In the second proximal state, the chamber 18 is open, the top 14 is separated from the opening 17, and then opened. Furthermore, the above-mentioned sealing is maintained.

According to the applications and the requirements, the chamber 18 can be sterile or non-sterile, wet or dry, based on the probe 3a. For example, a pH probe requires a moist environment. This moist environment is obtained by the presence, in the chamber 18, of an ad hoc liquid, injected at the time of storage and for this reason referred to as "storage liquid."

In the case where, on the contrary, the probe 3a does not require a moist environment but a dry environment, as in the case where the accessory 3 is a tube, such a storage liquid is not provided.

The chamber 18 can, after mounting the connecting device 1 that is provided with the accessory 3 and drainage of air (or gas) that is located therein, fill as a function of housing the active proximal part 9 there on the inside or placing it there on the periphery, as it was described.

The chamber 18 can also fulfill one or more other functions, in connection with the desired usages.

A possible function of the chamber 18 is to put in it a storage liquid, as it was disclosed, such as potassium chloride or a potassium chloride solution. Then, it is possible to initiate sterilization, for example gamma-ray sterilization.

Another possible function of the chamber 18, in the case where the accessory 3 is a probe 3a, is to initiate a calibration of the latter. For this purpose, a calibration liquid is put into the chamber 18.

Another possible function of the chamber 18, in the case where the accessory 3 is a tube 3b, is to constitute a chamber that is closed in an airtight way in which the tube 3b is placed on standby for use.

The mounting process of the connecting device 1 and the accessory 3, and, if necessary, the functional part 11, on a receptacle 2 is implemented as follows on the production site, in particular under "clean room" conditions.

A start is made from a situation where a receptacle 2, devoid of contents, the accessory 3, if necessary the functional part 11, and finally constituent elements 15, 16 and 17 of the connecting device 1 are used.

The description of the mounting and the production is made in the case of a flexible and disposable receptacle 2 such as a so-called 2D pocket or a so-called 3D foldable pocket.

On the one hand, in a preliminary stage, the first element 15 is attached rigidly to the receptacle at the location of the opening 17 by thermal welding or in another analogous manner.

On the other hand, in another preliminary stage, the accessory 3 is inserted into the third element 17, it is positioned axially in a suitable way, and it is attached rigidly to the latter at the location of the first and second rings 39 and 40, if necessary in the bore 45. If necessary, also, the functional part 11 is inserted, positioned and attached. This insertion is carried out by relative axial sliding, from the distal end of the second ring 40 and toward the top 14. By this stage, the first step is to constitute the chamber 18.

Then, in a second stage subsequent to this other preliminary stage, the unit that consists of third element 17+accessory 3 and optionally functional part 11 is mounted on and in the second element 16. This mounting is implemented by relative axial sliding of said unit 17, 3 in the second element 16 from its proximal end 25 and toward its distal end 26. It is advisable, of course, to do this in such a way that the distal part 10 of the accessory 3 and the means such as the electrical conductor, tube, . . . that are associated therewith, and, if necessary, the distal part 13 of the functional part 11, pass through the totally open distal end 24 of the second element 16 or the openings 27a and 27b that are provided for this purpose.

Then, in a third stage that is subsequent to this second stage, the unit that consists of second element 16+third element 17+accessory 3 and optionally functional part 11 is mounted on and in the first element 15. This mounting is implemented by relative axial sliding of said unit 16, 17, 3 into the first element 15 starting from its distal end 21 toward its proximal end 20 into the angular position that is defined by the guide 28, 29. The introduction of the top 14 into the open distal end is made possible using the elastic deformability of the top. The sliding is continued until the slot(s) 30 and lug(s) 31 work together corresponding to the first distal state. The end of travel is then reached barring specific action for the purpose of releasing the slot(s) 30 and lug(s) 31, whereby their cooperation is ensured because of the elastic foot or feet 32. By this stage, the composition of the chamber 18 is finished, and then the chamber is closed in an airtight manner.

The unit that consists of connecting device 1+accessory 3+optionally functional part 11 is then in place, in the first distal state, whereby the receptacle 2 is devoid of contents. The chamber 18 is then devoid of contents other than the ambient atmosphere in which the connecting device 1 was mounted on the receptacle 2.

When this is desired, using a syringe that is connected either to the end fitting of the distal end part 13 of the functional part 11, in the case where the accessory 3 is a probe 3a, or on the distal end 10 of the accessory 3, in the case where the accessory 3 is a tube 3b, the air (or gas) that is located in the chamber 18 is drawn in, and it is drained from the latter. Next, the syringe is disconnected and removed.

Then, it is possible, using a syringe that is connected as above, to inject into the chamber 18 a storage liquid, such as potassium chloride or a potassium chloride solution. Next, the syringe is disconnected and removed. Such an embodiment is imposed when the accessory 3 is a probe 3a that should be kept in a moist environment, as is the case of a pH probe. If, on the contrary, the accessory 3 is a probe 3a that should be kept in a dry environment, as is the case of a colorimetry probe, the injection of storage liquid is not provided.

Then, it is possible to initiate a sterilization of the unit that consists of receptacle 2+connecting device 1+accessory 3+, if necessary, the functional part 11, for example a gamma ray sterilization.

The different stages of the process for mounting the connecting device 1 and the accessory 3, and, if necessary, the functional part 11, on a receptacle 2 that were just described are implemented most often one after the other at a site for the production of functional containers 5.

The second unit that consists of folded receptacle 2+connecting device 1+accessory 3+, and, if necessary, the functional part 11 forms a flat unit that can then be packaged, for example, in a first plastic pocket that is itself placed in a packaging box.

The second unit that consists of receptacle 2+connecting device 1+accessory 3+, if necessary, the functional part 11 can then be stored and shipped until used, with the latter taking place at a site of use that is generally different from the production site of the functional containers 5 and a certain time after the production has taken place, whereby asepsis is preserved.

The process for implementation of the second unit that consists of receptacle 2+connecting device 1+accessory 3+, if necessary, the functional part 11+the possible rigid means for holding the receptacle 2 from the outside if the latter is flexible, on the site of use, is implemented as follows, once the packaging box and the pocket that have served as packaging are completely unpacked.

This process of implementation comprises operating stages that are linked to the receptacle 2, in itself, independently of the fact that it is connected to the connecting device 1 and to the accessory 3 and, if necessary, to the functional part 11. These operating stages comprise the following:

Placing the receptacle 2, if it is a flexible receptacle 2, in the rigid means for holding from the outside, provided that it is necessary (the case of a 3D pocket).

Filling the receptacle 2 with the contents.

Implementing any suitable treatment on the contents of the receptacle 2, such as reaction, mixing, aeration, and addition of other components, . . . .

Optionally shipping or storing the receptacle 2 and its contents in a temporary way.

Draining the receptacle 2 of its contents so as to use the latter.

These operating stages are within the grasp of one skilled in the art and do not have to be described.

The process for implementation further comprises operating stages that are linked specifically to the connecting device 1, to the accessory 3, and, if necessary, to the functional part 11.

These operating stages are as follows:

In a preliminary stage, draining the chamber 18 of storage liquid provided that such a storage liquid has been put there during production and, in this case, if necessary, rinsing the chamber 18, or if not, not carrying out this preliminary stage.

First, passing the unit that consists of connecting device 1+accessory 3+, if necessary, the functional part 11 from the first distal state, in which it was found at the end of the production, to the second proximal state.

Then, implementing the accessory 3.

In one embodiment, the process also comprises an additional operation for regulating, monitoring or calibrating the accessory 3.

In a particular embodiment that corresponds to the case where the accessory 3 is a probe 3a that is to be stored in a moist environment (for example, a pH probe) and that requires such an additional operation for regulating, monitoring, or calibrating the accessory 3, the sequence is as follows:

Draining from the chamber 18 the storage liquid that was put there during production, and, if necessary, rinsing the chamber 18.

Executing an operation for regulating, monitoring or calibrating the probe 3a.

Placing the receptacle 2, if it is a flexible receptacle 2, in rigid means for holding from the outside.

Draining the receptacle 2 with the contents.

Passing the unit that consists of connecting device 1+probe 3a+tube 11 from the first distal state in which it was found at the end of the production to the second proximal state.

Implementing any suitable treatment on the contents of the receptacle 2, such as reaction, mixing, aeration, and addition of other components, . . . .

Using the probe 3a by continuing to implement suitable treatment on the contents.

Implementing another operation of regulating, monitoring or calibrating the probe 3a.

Optionally, shipping or storing the receptacle 2 and its contents temporarily.

Ultimately, draining the receptacle 2 of its contents so as to use the latter.

This sequence of stages does not rule out others, however.

The operating stages that are linked specifically to the connecting device 1 and to the accessory 3 are now described in the particular embodiment where the accessory 3 is a probe 3a that requires an additional operation for regulating, monitoring or calibrating the accessory 3 and where the functional part 11 is an intake and drainage tube. The other embodiments of these stages can be deduced from this particular embodiment.

Regarding the stage that consists in draining from the chamber 18 the storage liquid that was put there during the production, the procedure is as follows.

Using a syringe that is connected to the end fitting of the distal end part 13 of the tube 11, the storage liquid that is found in the chamber 18 is drawn in and then drained from the latter. Next, the syringe is disconnected and removed.

Regarding the stage that consists in passing the unit that consists of connecting device 1+probe 3a+tube 11 from the first distal state, in which it was found at the end of the production, to the second proximal state, the procedure is as follows.

The unit that consists of second element 16+third element 17+accessory 3+tube 11 is slid axially over the course C in the proximal direction, i.e., toward the receptacle 2, until the slot(s) 30 and lug(s) 31 work together corresponding to the second proximal state. The end of travel is then reached.

The switching of the cooperation of the slot(s) 30 and lug(s) 31 corresponding to the first distal state to their cooperation corresponding to the second proximal state is made possible because of the flexibility of the foot or feet 32.

To make possible the withdrawal movement for disengagement of a lug 31 from a slot, a tool (not shown) that can move the lug 31 against the foot 32 is used.

When, by the single movement that was just described, the operation moves from the first distal state to the second proximal state, the channel 22 that was until then closed in an airtight manner by the top 14 is opened, and the proximal active part 9a of the probe 3a is put into communication with the inside 4, whereby this proximal active part 9a is thus inserted into the receptacle 2, as was indicated above. The chamber 18 that was heretofore closed is opened, and if the receptacle 2 contains contents exceeding the level of the opening 7, these contents can fill the chamber 18. The proximal active part 9a is also in contact or in communication with these contents.

In the second proximal state, the top 14 fulfills its protective function, while the first ring 39 ensures the sealing of the receptacle 2.

The connecting device 1 is reversible in that it is possible to make it go back from the second proximal state to the first distal state by a movement that is opposite to the one described above for passing from the first distal state to the second proximal state.

This operation makes it possible to measure the contents of the receptacle 2 in the chamber 18, which was closed.

Regarding the stage itself for implementing the probe 3a, i.e., for measuring by the latter the parameter to which it is adapted, it is within the grasp of one skilled in the art and does not have to be described.

Regarding the stage that consists in the additional operation for regulating, monitoring or calibrating the probe 3a, the procedure is as follows.

This stage, now conventionally referred to as "calibration," can be implemented a single time or, on the contrary, several times, and it can be implemented at different times and for several purposes.

In one embodiment, there are two calibrations:

An initial calibration, before the receptacle 2 is filled with its contents. The purpose of this calibration is to ensure that the probe 3a is correctly regulated and, failing this, to regulate it in a suitable manner.

A final calibration, after the receptacle 2 has been drained of its contents. This calibration is done for purposes of checking that the probe 3a has not become out of adjustment during the process.

If necessary, it is possible to consider one (and even several) intermediate calibration(s) after the receptacle 2 has been filled (totally or partially) with its contents and before it has been drained of its contents. The purpose of such a calibration is to ensure, during the process, that the probe 3a is correctly regulated and, lacking this, regulating it in a suitable manner.

The calibration is implemented by means of the chamber 18, of which it is one of the functions.

In all of the cases, the calibration is implemented whereas the unit that consists of connecting device 1+probe 3a+tube 11 is in the first distal state and whereas the chamber 18 is closed in an airtight manner. Either the unit that consists of connecting device 1+probe 3a+tube 11 is in the first distal state for the reason that it was there previously, for example at the end of production, or this unit is brought into the first distal state from the second proximal state in which it was found previously. This is possible because the connecting device 1 is reversible.

The presence of the chamber 18 allows an on-line calibration in that it can be implemented, whereas the device 1, the probe 3a and the tube 11 have already been connected to the receptacle 2.

Having been, as indicated, in the first distal state, first a pH solution is injected for calibration into the chamber 18 that is closed in an airtight manner, using a syringe without a needle, via the tube 11 by means of the connection end fitting of the distal part 13. Once the injection is terminated, the syringe is withdrawn from the connection end fitting.

Then, with the pH solution for calibration thus filling the chamber 18 that is still closed in an airtight manner, and with the active proximal part 9a being in contact with the pH solution for calibration, the probe 3a is calibrated if necessary and as required.

Then, with the chamber 18 still closed in an airtight manner, the pH solution for calibration is drained using a syringe without a needle via a drainage tube 11 by means of the connection end fitting at the distal part 13. Once the drainage has ended, the syringe is removed from the connection end fitting.

The rinsing syringe that contains a rinsing product such as sterile water is then connected to the tube 11 by means of the connection end fitting. The rinsing product is injected into the chamber 18, and then it is drained off.

The calibration operation having been thus carried out, it is possible to open the chamber 18 by passing from the first distal state into the second proximal state. The probe 3a can then measure the parameter for which it is intended in the receptacle 2, and more especially its contents.

The invention claimed is:

1. A device for connection to a receptacle of an accessory having an active proximal part that is able to be in put into communication with an inside of the receptacle by an opening of the receptacle, the device comprising:
   a first element ensuring the rigid attachment of the connecting device to the receptacle, defining a channel between the inside and an outside of the receptacle, serving as a support for the second element and an axial movement guide on an axial course of which two ends of travel correspond to a first distal state and to a second proximal state, helping to serve as a guide for the third element, and helping to delimit the chamber;
   a second element serving as a support to the third element that is attached rigidly to the second element, and forming a moving, axially sliding element on the course whose two ends of travel correspond to the first distal state and the second proximal state;
   a third element, to which a base, a body, and a top belongs, serving as a support to the accessory that is attached rigidly to the third element, forming a moving, axially sliding element on the course whose two ends of travel correspond to the first distal state and the second proximal state, ensuring, using the top, the airtight closing of the opening in the first distal state, ensuring, using the top, a protection of the active proximal part in the second proximal state, and helping to delimit the chamber,
   the top closing the first element in an airtight manner in the first distal state and helping to protect the active proximal part in the second proximal state, the base serving as a support to the accessory that is attached rigidly to the base, ensuring the guiding of the sliding of the third element on and relative to the first element with sealing, and helping to delimit the chamber, the base comprising:
- at least a first ring in a proximal end part thereof and configured to be able to slide axially, by an outside surface, on and along an inside surface of the tubular wall with sealing, and
- a second ring at a distal end part thereof configured to be attached rigidly by an outside surface thereof on and against the inside surface of the tubular wall of the second element, inside surfaces of the rings being configured to enable the rigid attachment of the accessory with sealing, and the body comprising a connecting part that is provided with a bore in which the accessory is inserted, and at least one carrying element rigidly connecting the top and the base; and a chamber closed in an airtight manner in the first distal state and in communication with the inside in the second proximal state, the chamber housing the active proximal part inside or placing the active proximal part on a periphery thereof, and one or more of putting a storage liquid therein, and putting a liquid for regulating, monitoring or calibrating the accessory therein or constituting a chamber that is closed in an airtight manner in which the accessory is placed on standby for use.

2. The connecting device according to claim 1, wherein a relative position of the third element relative to the second element is stationary, with the second ring and the connecting part being located in the second element, and with the first ring, the carrying elements, and the top being located outside of the second element.

3. The connecting device according to claim 1, wherein the chamber is limited at two axial end parts thereof by a distal transverse surface of the wall that forms the top and by a transverse surface of the proximal end of the first ring and by the chamber being limited at a periphery thereof by the inside surface of the tubular wall of the first element.

4. The connecting device according to claim 3, wherein the sealing of the chamber, in the first distal state is ensured by the sealing between the top and a seat thereof that belongs to the first element, by the sealing between the first ring and the inside surface of the tubular wall, and by the sealing between the accessory and the third element.

5. A device for connection to a receptacle of an accessory having an active proximal part that is able to be in put into communication with an inside of the receptacle by an opening of the receptacle, the device comprising:
- a first element ensuring the rigid attachment of the connecting device to the receptacle, defining a channel between the inside and an outside of the receptacle, serving as a support for the second element and an axial movement guide on an axial course of which two ends of travel correspond to a first distal state and to a second proximal state, helping to serve as a guide for the third element, and helping to delimit the chamber;
- a second element serving as a support to the third element that is attached rigidly to the second element, and forming a moving, axially sliding element on the course whose two ends of travel correspond to the first distal state and the second proximal state;
- a third element, to which a top belongs, serving as a support to the accessory that is attached rigidly to the third element, forming a moving, axially sliding element on the course whose two ends of travel correspond to the first distal state and the second proximal state, ensuring, using the top, the airtight closing of the opening in the first distal state, ensuring, using the top, a protection of the active proximal part in the second proximal state, and helping to delimit the chamber; and
- a chamber closed in an airtight manner in the first distal state and in communication with the inside in the second proximal state, the chamber housing the active proximal part inside or placing the active proximal part on a periphery thereof, and one or more of putting a storage liquid therein, and putting a liquid for regulating, monitoring or calibrating the accessory therein or constituting a chamber that is closed in an airtight manner in which the accessory is placed on standby for use, wherein in the first distal state, the second element is laterally opposite the first element, without being opposite a part of the first element that is adjacent to a proximal end thereof, a part of the second element projecting from a distal end of the first element, and in the second proximal state, the second element is laterally completely opposite the first element toward the distal end thereof, without being opposite an axially shorter part of the first element that is adjacent to the proximal end thereof.

6. A device for connection to a receptacle of an accessory having an active proximal part that is able to be in put into communication with an inside of the receptacle by an opening of the receptacle, the device comprising:
- a first element ensuring the rigid attachment of the connecting device to the receptacle, defining a channel between the inside and an outside of the receptacle, serving as a support for the second element and an axial movement guide on an axial course of which two ends of travel correspond to a first distal state and to a second proximal state, helping to serve as a guide for the third element, and helping to delimit the chamber, the first element comprising a tubular wall having a proximal end provided with a flange for attachment to the receptacle;
- a second element serving as a support to the third element that is attached rigidly to the second element, and forming a moving, axially sliding element on the course whose two ends of travel correspond to the first distal state and the second proximal state, the second element comprising a tubular wall, inserted into the first element, an inside surface of the tubular wall of the first element and an outside surface of the tubular wall of the second element comprising a combination of retractable slots and lugs that are arranged radially and are able to cooperate, forming removable means for end-of-travel locking of axial movement of the second element on and relative to the first element on the course; and
- a third element, to which a top belongs, serving as a support to the accessory that is attached rigidly to the third element, forming a moving, axially sliding element on the course whose two ends of travel correspond to the first distal state and the second proximal state, ensuring, using the top, the airtight closing of the opening in the first distal state, ensuring, using the top, a protection of the active proximal part in the second proximal state, and helping to delimit the chamber; and
- a chamber closed in an airtight manner in the first distal state and in communication with the inside in the second proximal state, the chamber housing the active proximal part inside or placing the active proximal part on a periphery thereof, and one or more of putting a storage liquid therein, and putting a liquid for regulating, monitoring or calibrating the accessory therein or constituting a chamber that is closed in an airtight manner in which the accessory is placed on standby for use.

7. The connecting device according to claim 6, wherein a lug is arranged so as to be radially elastically stressed outward toward the bottom of an opposing slot so as to be housed at the bottom of the opposing slot and so as to be able to be retracted from a slot with which the lug worked, and to radially elastically withdraw toward an inside to be able to slide on the opposing surface of the element carrying the slots.

8. The connecting device according to claim 6, wherein the inside surface of the tubular wall of the first element and the outside surface of the tubular wall of the second element comprise a combination of an axial groove and a radial projection toward an outside that forms a guide.

9. A device for connection to a receptacle of an accessory having an active proximal part that is able to be in put into communication with an inside of the receptacle by an opening of the receptacle, the device comprising:

a first element ensuring the rigid attachment of the connecting device to the receptacle, defining a channel between the inside and an outside of the receptacle, serving as a support for the second element and an axial movement guide on an axial course of which two ends of travel correspond to a first distal state and to a second proximal state, helping to serve as a guide for the third element, and helping to delimit the chamber;

a second element serving as a support to the third element that is attached rigidly to the second element, and forming a moving, axially sliding element on the course whose two ends of travel correspond to the first distal state and the second proximal state;

a third element, to which a base, a body, and a top belongs, serving as a support to the accessory that is attached rigidly to the third element, forming a moving, axially sliding element on the course whose two ends of travel correspond to the first distal state and the second proximal state, ensuring, using the top, the airtight closing of the opening in the first distal state, ensuring, using the top, a protection of the active proximal part in the second proximal state, and helping to delimit the chamber, the top closing the first element in an airtight manner in the first distal state and helping to protect the active proximal part in the second proximal state, the base serving as a support to the accessory that is attached rigidly to the base, ensuring the guiding of the sliding of the third element on and relative to the first element with sealing, and helping to delimit the chamber, the base including one or more rings, and the body comprising a connecting part that is provided with a bore in which the accessory is inserted, and at least one carrying element rigidly connecting the top and the base; and a chamber closed in an airtight manner in the first distal state and in communication with the inside in the second proximal state, the chamber housing the active proximal part inside or placing the active proximal part on a periphery thereof, and one or more of putting a storage liquid therein, and putting a liquid for regulating, monitoring or calibrating the accessory therein or constituting a chamber that is closed in an airtight manner in which the accessory is placed on standby for use wherein the one or more rings comprise channels configured to allow mounting inside and rigid attachment of a functional part with sealing.

\* \* \* \* \*